United States Patent [19]

Masilamani et al.

[11] Patent Number: 4,647,686

[45] Date of Patent: Mar. 3, 1987

[54] CATALYTIC METHOD OF PREPARING KETO-CYANO ALKANE COMPOUNDS

[75] Inventors: Divakaran Masilamani, Morristown; Edward H. Manahan, Morris Plains, both of N.J.

[73] Assignee: Allied Corporation, Morris Township, Morris County, N.J.

[21] Appl. No.: 297,658

[22] Filed: Aug. 31, 1981

[51] Int. Cl.$^4$ .......................................... C07C 120/00
[52] U.S. Cl. ...................................... 558/315; 558/319
[58] Field of Search ............ 260/465.1, 465 R, 465.6, 260/465 F; 558/315

[56] References Cited

U.S. PATENT DOCUMENTS

| | | | |
|---|---|---|---|
| 2,710,302 | 6/1955 | Hyson | 260/465.1 X |
| 2,770,643 | 11/1956 | Anderson | 260/465.1 |
| 3,387,026 | 6/1968 | Chafetz et al. | 562/508 |
| 3,517,047 | 6/1970 | Ohno et al. | 260/465.1 X |
| 4,097,517 | 6/1978 | Rogic et al. | 260/465.1 X |

FOREIGN PATENT DOCUMENTS

| | | | |
|---|---|---|---|
| 42-7772 | 3/1967 | Japan | 260/465.1 |
| 42-8289 | 4/1967 | Japan | 260/465.1 |
| 45-32688 | 4/1967 | Japan | 260/465.1 |
| 42-13089 | 7/1967 | Japan | 260/465.1 |
| 43-15962 | 7/1968 | Japan | 260/465.1 |

OTHER PUBLICATIONS

Fieser et al., "Reagents for Organic Synthesis", vol. 3, (Wiley–Interscience–N.Y.), p. 214.

Primary Examiner—Joseph Paul Brust
Attorney, Agent, or Firm—Richard C. Stewart; Gerhard H. Fuchs

[57] ABSTRACT

This invention relates to a process for preparing keto-cyano alkane compounds by treating the corresponding alpha substituted cycloalkanone compound with oxygen and ammonia in the presence of a transition metal catalyst.

14 Claims, No Drawings

CATALYTIC METHOD OF PREPARING KETO-CYANO ALKANE COMPOUNDS

BACKGROUND OF THE INVENTION

1. Field of the Invention

This invention relates to a process of preparing keto-cyano alkane compounds, which are useful as intermediates in the preparation of other valuable derivatized keto-alkane compounds. More particularly, this invention relates to a catalytic process for preparing such compounds from the corresponding cycloalkanone compound.

2. Brief Description of the Prior Art

Keto-cyanoalkane derivatives, are useful compounds having varied uses in commercial applications. For example, keto carboxylic acid esters, amides and N-substituted amides are useful as detergent-dispersants for lubricating oils, particularly when in combination with aromatic sulfonates. Several methods are disclosed in the prior art for preparing such derivatives. U.S. Pat. No. 3,387,026 discloses that these derivatives can be prepared from the corresponding keto-carboxylic acid, which, in turn, is prepared from the corresponding alpha-alkyl cycloalkanone compound. In this method, the keto acid was prepared by the selective oxidation of the corresponding alpha hydrocarbon substituted cyclohexanone in the presence of an alkali metal fluoride catalyst. In another of such methods, the keto-carboxylic acid is prepared by heating the corresponding alpha-alkylcyclohexanone in the presence of chromic oxide and sulfuric acid.

Each of these prior art processes provides several adverse effects. For example, the later process, through effective in producing the keto carboxylic acid, has the undesirable aspect of producing the desired product in low yields, and requiring expensive equipment and special handling for the highly corrosive chromic oxide/sulfuric acid combination.

SUMMARY OF THE INVENTION

In accordance with this invention there is provided a process for preparing a keto-cyano-alkane compound of the formula:

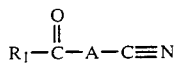

which comprises contacting a cycloalkanone compound of the formula:

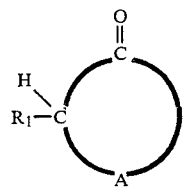

oxygen and ammonia in the presence of a catalytically effective amount of transition metal cations.

In the above structural formula:

$R_1$ is nitro, lower alkyl, lower alkoxy, lower alkoxyalkyl, phenyl, lower alkylphenyl, lower haloalkyl, amino, lower mono- and dialkylamino, or lower alkanoyl. As used herein the term "lower" denotes no more than seven aliphatic carbon atoms.

A is a straight or branched alkylene chain having from about 3 to about 15 carbon atoms completing a 5, 6, 7 or 8 membered monocylic ring structure. Optionally "A", may be unsubstituted or substituted with one or more "inert substituents", which as used herein are substituents which are inert under the conditions of the reaction, i.e. do not themselves enter into the reaction or otherwise interfer in a substantial way with the desired course of the reaction.

Compounds prepared in accordance with the process of this invention are useful as intermediates in the preparation of other useful compounds. For example, an appropriate keto-cyano alkane compound can be contacted with water to form the corresponding keto carboxylic acid amide which can be used as detergent/dispersants for lubricating oils. Similarly, the keto-cyanoalkane compound can be hydrolyzed in the presence of either, acid or base, to form the corresponding keto carboxylic acid. As indicated hereinabove these keto carboxylic acid derivatives are also useful compounds. The above described reactions of cyano functions are well known in the prior art and will not be described herein in detail.

DESCRIPTION OF THE PREFERRED EMBODIMENTS

The process of this invention can be depicted schematically by the following Reaction Scheme A in which $R_1$ and A are as described herein above, and M is a transition metal cation:

Reaction Scheme A

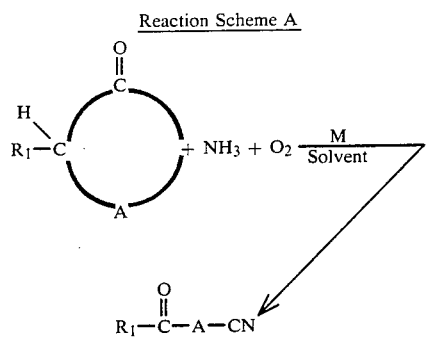

It should be appreciated that the above reaction scheme is only intended to depict a gross or overall scheme, because there are possibly various other equilibria involved under the reaction conditions which are intended to be employed in the process of this invention.

In carrying out the reaction of the above reaction scheme, preferably stiochiometric amounts of the cycloalkanone compound, ammonia and oxygen are contacted preferably in a "suitable inert solvent" in the presence of a "catalytically effective" amount of a suitable metal catalyst. While the scheme does depict stiochiometric amounts of the reactants, it should be appreciated that excesses of one or more of the various reactants can be employed. Excesses of the gaseous reactants do not adversely affect the reaction or the isolation of the final product in relatively pure form, because these excesses are easily disposed of through gaseous evolution. However, in those instances where one or more of the reactants are solids or liquids, an excess of these reactants may adversely affect the isolation of the final product in relatively pure form because of potential problems in separating the product from the unreacted reactant(s).

The manner in which the reactants are contacted is not critical. Accordingly, the reactants, catalyst and reaction solvent can be contacted in any order, order of addition also not being critical. Normally, the cycloalkanone compound, ammonia and catalyst are added to a solvent, into which oxygen, preferably alone, but also in combination with other inert gases, such as nitrogen, helium, argon, and neon, has been added. The addition of oxygen to the solvent is continued throughout and after the addition of the other reactants. The oxygen can be added merely by exposing the reaction mixture to the open atmosphere, or more elaborate procedures may be employed. For example, the oxygen can be bubbled into the mixture contained in an appropriate closed vessel in which an oxygen atmosphere can be maintained. Oxygen uptake can also be measured by a buret. Such a procedure would allow the course of the reaction to be monitored. Also, the addition of oxygen can be carried out with agitation, as for example with a magnetic or mechanical stirrer. Stirring increases the solvation of oxygen and ammonia, and accordingly it increases the rate of reaction.

The ammonia can be added to the reaction mixture directly from the gaseous phase, as for example through the use of a bubbler in much the same manner as the addition of the oxygen. The ammonia can also be added in the form of a pre-formed solution in which the desired quantity of ammonia has been dissolved beforehand.

Cycloalkanone compounds which are useful in the conduct of the process of this invention are compounds of the formula:

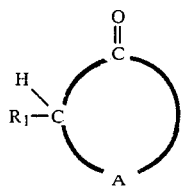

wherein "A" and "$R_1$" are as described hereinabove. Compounds which are representative of such compounds are as follows:

Cyclopentanone compounds of the formula:

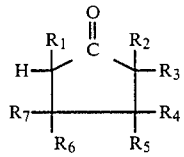

Cyclohexanone compounds of the formula:

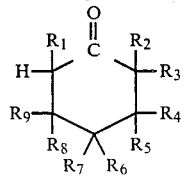

Cycloheptanone compounds of the formula:

-continued

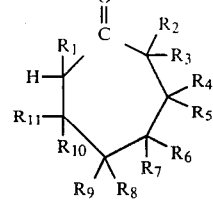

Cycloctanone compounds of the formula:

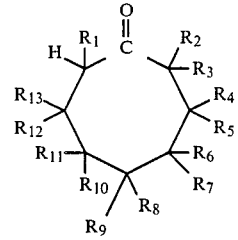

In the above generic formulas, $R_1$ is as described herein above, and $R_2$ through $R_{13}$, are the same or different, and are selected from the group consisting of hydrogen, and $R_1$. Illustrative of useful and preferred $R_1$ substituents are phenyl; lower alkyl groups i.e. alkyl having from 1 to 7 carbon atoms, such as methyl, ethyl, propyl, butyl, pentyl, hexyl and isomeric forms thereof; lower alkoxy i.e. alkoxy having from 1 to 7 carbon atoms such as methoxy, ethoxy, propoxy, butoxy, pentoxy, hexyloxy and isomeric forms thereof; nitro; halo, such as chloro, bromo and fluoro; lower alkanoyl, such as acetyl; lower alkaryalkyl; lower alkoxyalkyl having up to 7 carbon atoms, such as methoxymethyl, ethoxymethyl, methoxyethyl, propoxymethyl and the like; lower mono-or dialkylaminoalkyl, such as dimethylaminoethyl; amino; lower di-and mono-alkylamino and like inert substituents. It should be appreciated that the above listing of inert substituents is not intended to be exhaustive of suitable inert substituents, but is merely intended to be illustrative of useful substituents to enable one of skill in the art to practice the entire invention without undue experimentation.

In the preferred embodiments of this invention, the cycloalkanone reactants are symmetrical compounds wherein:

$R_1$ is isopropyl, methyl, propyl, ethyl, methoxy, ethoxy, chloro, bromo, fluoro, amino, dimethylaminomethyl, or acetyl; and A is a divalent radical of the formula:

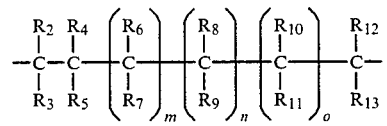

wherein:

n, m and o or individually 1 or 0; and $R_2$ to $R_{13}$ are individually hydrogen, lower alkyl, lower alkoxy or phenyl, wherein no more than three of said $R_2$ to $R_{13}$ substituents are other than hydrogen.

In the particularly preferred embodiments of this invention:

$R_1$ is methyl, ethyl or propyl; and

A is as described hereinabove wherein $R_2$ to $R_{13}$ are hydrogen, methyl, ethyl, methoxy, ethoxy or phenyl with the proviso that no more than two of said $R_2$ to $R_{13}$ substituents are other than hydrogen. Illustrative of compounds falling within the scope of the above generic description are 2,3,4-trimethyl cyclohexanone; 2,4-dimethylicyclooctanone, 2-methylcyclohexanone; 2,5-dimethylcycloheptanone; 2,4-dimethylcyclohexanone, 2-butylcyclohexanone; 2-acetylcyclohexanone, 8-isobutylcycloctanone, 2,3,4-trichlorocyclohexanone; 2,6-dibromocyclohexanone, 2,5-dimethylcyclohexanone; 2-(dimethylaminoethyl)cyclohexanone; 2-aminocyclohexanone; 2-isopropyl-cyclohexanone; 2-propylcyclohexanone; 2-methylcyclopentanone; 2-aminocycloheptanone; 3-bromo-2-amino -cycloheptanone; 2-methoxy-4-isopropyl cycloheptanone; 2-methoxy cycloheptanone; 2-nitro-4-methyl cycloheptanone and like pounds. Cycloalkanone compounds, such as cyclohexanone, cycloheptanone, cyclopentanone and cyclooctanone having a methyl group substituted at one or both of the carbon atoms alpha to the keto junction are particularly preferred, and amongst these cyclohexanone is the most preferred reactant in the process of this invention. As will be apparent from the examples set forth hereinbelow, when cyclohexanone is employed as the cycloalkanone reactant outstanding yields of the desired ketocyano alkane compound can be obtained with appropriate manipulation of reaction parameters.

Cycloalkanone compounds which are useful as intermediates in the practice of this invention can be obtained from a number of sources. Such compounds can be obtained from commercial sources. For example, substituted and unsubstituted cyclohexanone, cyclopentanone, cycloheptanone and cyclooctanone are commercially available from commercial sources such as Aldrich Chemical Company.

The aforementioned compounds, and other useful cycloalkanone compounds can also be prepared in accordance with known preparative procedures. For example various substituted and unsubstituted cyclohexanone, cyclopentanone, cycloheptanone and cyclooctanone precursors can be prepared in accordance with the procedures described in detail in Migrdichian, Vartkas, "Organic Synthesis, Vols. 1 and 2 Reinhold Publishing Corporation, New York (1957).

The process of this invention is carried out in the presence of an "effective transition metal cation catalyst" As defined herein, "effective transition metal cation catalyst" is a transition metal cation which is effective for initiating or catalyzing the reaction. It is believed that the catalyst functions as a solvated transition metal cation in the reaction solvent. The cation can exist in the "free form", i.e. as the solvated cation or it can exist in other forms wherein the cation is complexed with an organic solvent in adduct form or as a complex with a chelating agent for said cation. For example, it is believed that the cation can exist as an etherate, complexed with one mole of a suitable ether per mole of composition. It is believed that the cation can also form adducts with aromatic hydrocarbons, such as naphthalene and toluene and chelates with cation chelating agents, such as pyridine, hexacyclen, the nitrogen analog of 18-crown-6-crown ether; tertiary amines, such as N,N,N, N'''-tetramethylethylenediamine; crown ethers, e.g., 15-crown-5-crown ether, 18-crown-6-crown ether, cryptates, which are bicyclic nitrogen bridged diamines having oxyethylene bridges, such as 2.2.2-crypt, and the like. Adducts and chelates comprising the cation, in some cases, may display better crystalline properties than the free-form of the cation, and therefore may be more convenient for handling and operability. In addition, the chelated cation may significantly influence the catalytic activity during the reaction due to marked differences in ion pairing phenomena. Also chelating agents increase the solubility of the cation which usually results in accelerated rates of reaction. However, for the purposes of this invention, the free form of the cation and the solubility of the catalyst which usually results in accelerated rates of reaction. However, for purposes of this invention, the free-form catalytic composition and adducts and chelates thereof, are considered to be equivalents and within the scope of applicable catalytic cations.

The reaction is carried out in the presence of a "catalytically effective amount" of the transition metal cation. As defined herein, "a catalytically effective amount" refers to an amount of the cation sufficient under the reaction conditions, i.e. pressure, temperature, solvent, etc., to initiate the reaction. In the preferred embodiments of this invention, the reaction can be initiated by as little as 0.01 mole percent of the catalyst based on the total weight of the cycloalkanone reactant. In the particularly preferred embodiments of this invention, the quantity of catalyst employed is at least 1 mole percent base on the total weight of the cycloalkanone reactant. Larger quantities of catalyst do not appear to adversely affect the reaction. However, because of the high cost of certain useful catalyst, their use is limited by economics.

Catalytic cations which can be employed in the process of this invention can be derived from transition metal salts which are sufficiently soluble in the reaction solvent under the reaction conditions employed so as to provide a "catalytically effective amount" of the catalyst cation in solution in the free form or as adducts and chelates thereof. Illustrative of preferred transition metal salts are the acetate, octanoate, stearate, sulfate, nitrate, halide, hydroxide, phosphate, carbonate, oxide and like salts of transition metals such as copper, iron, nickel, cobalt, platinum, palladium and the like. These salts may be in the hydrated form or in the anhydrous form. While the above mentioned salts generally are utilizable under the appropriate reaction conditions to form the desired keto cyano alkane compound, as is usually the case in any large group or class, one or more members of the sub-group or sub-class, for one reason or another, are particularly preferred, compared to the class as a whole. In the instant case, the particular catalytic cation preferred for use under the preferred reaction conditions is cupric cation which is preferably derived from the cupric salts of aliphatic or aromatic carboxylic acids, such as cupric acetate, cupric octanoate, cupric stearate, and cupric naphthalate, as well as, the cupric salts of mineral acids such as cupric chloride, cupric bromide, cupric nitrate and cupric sulfate.

Although the use of a reaction solvent in the process of this invention is not essential, particularly where the cycloalkanone reactant is liquid under the reaction conditions employed, an inert solvent is advantageously employed to facilitate contact between the reactants. The novel process of this invention can be run most readily in the presence of inert solvent in an amount sufficient to solubilize the reactants and a catalytically effective amount of the catalyst. Broadly speaking, any solvent or mixtures of solvents in which the cycloalkanone compound, oxygen, ammonia and a "catalytically effective amount" of the catalyst are soluble; which is inert under the conditions of the inventive process; and which does not otherwise interfere with the reaction can be employed as the reaction solvent. Illustrative of such solvents are hydroxy solvents as for example aliphatic alcohols such as methanol, ethanol, propanol, isopropanol, butanol and the like. Because of thier superior solubilizing properties when the process of this invention is conducted under preferred reaction conditions, methanol and ethanol are the reaction solvents of choice.

Reaction temperatures can be varied over a wide range as desired, provided that the reaction temperature is high enough to allow the reaction to proceed; low enough to prevent degradation of reactants and products; and low enough to allow solubilization of a sufficient quantity of gaseous oxygen. The reaction temperature may be conveniently varied within the range of from about 0° C. to about 200° C., depending on reaction conditions, reaction solvent, reactants, reaction product and other factors. In the preferred embodiment of this inventions the reaction is carried out at room temperature.

Similarly reaction pressures can be varied over a wide range as desired. For example, the reaction can be conveniently carried out at sub-atmospheric, atmospheric or super atmospheric pressure depending on the reaction conditions employed. However, for convenience the reaction is preferably carried out at autogenous pressure.

It will be apparent that manipulation of reaction temperatures, reaction pressures, and reaction solvents within the above described ranges can be carried out to maximize the rate and completeness of reaction and solubility of reactants. For example with a given cycloalkanone reactant and solvent, increased reaction temperature, i.e., above room temperature, will increase reaction rates and solvation of the catalyst, but will decrease the amount of solvated gaseous oxygen reactant. The result could be an overall decrease in the rate of reaction. Conversely, decreased reaction temperature, i.e. below room temperature, will decrease reaction rates and may adversely effect the solvation of the catalyst and solid reactants, while not affecting the degree to which oxygen is solubilized. Accordingly, in the practice of the preferred embodiments of this invention reaction pressures, temperatures and solvents will be manipulated as is necessary to obtain the best results. Usually when reaction temperatures are raised above room temperature for such purposes, as for example increasing the solubility of the solid reactants and catalyst, the reaction pressure may also be increased to maintain a sufficient quantity of the gaseous reactants in solution. Conversely, when reaction temperatures are lowered, the reaction pressure may also be lowered.

The reaction is preferably conducted for a period of time sufficient to provide the desired product. Reaction times are not critical and can be varied over a wide range as desired. Usually reaction times will depend on factors such as reaction conditions, i.e., reaction pressures and temperatures, reactants, solvents, catalysts and other factors known to those of skill in the art. Reaction times of up to 24 hours and more may be employed. In most instances, reaction times will vary from about 4 hours to about 24 hours under preferred reactions, and these reaction times represent the preferred range of reaction times.

The process of this invention is ordinarily performed as follows: A conveniently sized reactor fitted with an oxygen gas inlet or bubbler and stirring means is charged with a suitable solvent, such as methanol; a catalytically effective amount of a transition metal salt such as cupric chloride; a solution of ammonia in a solvent such as methanol; and a cycloalkanone such as 2-methylcyclohexanone to form a reaction mixture. The reaction mixture is then agitated as oxygen is bubbled into the reaction mixture for a time sufficent to convert the cycloalkanone and ammonia into the desired cyano-ketoalkane compound.

Work-up of the product mixture can be as follows, after oxygen uptake has substantially ceased, indicating completion of reaction, bubbling is discontinued. The reaction mixture containing the cyanoketo-alkane product, the catalyst, the solvent and some unreacted ammonia and cycloalkanone is stripped of volatiles and the residue taken up in ether. The ether solution is evaporated to dryness to provide the keto-cyano-alkane reaction product. The keto-cyanoalkane reaction product can be used as obtained, or further purified employing conventional purification techniques, such as distillation, solvent extraction, recrystallization and the like.

The keto-cyano-alkane compounds prepared in accordance with the process of this invention can be utilized as intermediates in the preparation of other useful compounds. For example such compounds can be used as intermediates in the preparation of useful keto carboxylic acid amides in accordance with the following reaction scheme B.

Reaction Scheme B

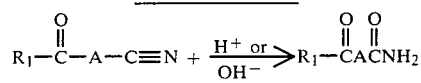

Similarly, each compounds can be treated with water in the presence of either acid or base to form the corresponding keto-carboxylic acid which, in turn, is treated with an arylalcohol or alkanol to form the correspondng keto-carboxylic ester in accordance with the following Reaction Scheme C:

Reaction Scheme C

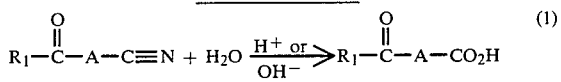 (1)

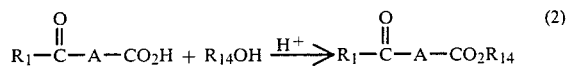 (2)

In the above Reaction Scheme C, $R_{14}$ is an aliphatic or aryl function. The above described reaction schemes, and the resulting products and their uses, are well known in the prior art and will not be described herein in detail.

The following specific examples are presented to more particularly illustrate the process of this invention, and should not be construed as being limitations on the scope and spirit of the invention.

EXAMPLE I

The Preparation of 1-Cyano-5-Ketohexane

A solution of 2 ml of $NH_3$ in 50 ml of methanol is charged into a round bottom flask fitted with a gas inlet tube and a mechanical stirrer. Fitted to the gas inlet tube is an oxygen buret graduated in mls and containing oxygen gas. To this solution is added with stirring 0.015 g of CuCl$_2$ 2H$_2$O and 1.1 g of 2-methyl cyclohexanone. Stirring was continued until all solids had dissolved. A steady stream of oxygen was bubbled into the solution for approximately 20 hours, while the solution was stirred at room temperature. Total oxygen uptake was 190 ml. The methanol solvent was removed by rotary evaporator and the product extracted in ether. The ether layer was concentrated. IR, NMR, and mass spectral analysis confirmed the presence of 1-cyano-5-ketohexane.

ANALYSIS

IR: —C≡N, 2245 cm$^{-1}$ and >C=O, 1715 cm$^{-1}$. No —OH peaks were observed

EXAMPLE II

The Preparation of 1-Cyano-1-Methyl-5-Ketohexane

A solution of 2 ml of NH$_3$ in 50 ml of methanol is charged into a round bottom flask fitted with a gas inlet tube and a mechanical stirrer. Fitted to the gas inlet tube is an oxygen buret graduated in mls and containing oxygen gas. To this solution is added with stirring 0.015 g of CuCl$_2$ 2H$_2$O and 1.5 g of 2,6-dimethyl cyclohexanone. Stirring is continued until all solids had dissolved. A steady stream of oxygen is bubbled into the solution for approximately 16 hours, while the solution is stirred at room temperature. Total oxygen uptake is 63 ml. The methanol solvent is removed by rotary evaporator and the product extracted in by rotary evaporator and the product extracted in ether. The ether layer is concentrated. IR and NMR analysis confirmed the presence of 1-cyano-1-methyl-5-ketohexane.

EXAMPLE III

The Preparation of 1-Cyano-2-Methyl-5-Ketohexane

A solution of 2 ml of NH$_3$ in 50 ml of methanol is charged into an airtight container fitted with a gas inlet tube and mechanical stirrer. To this solution is added with stirring 0.015 g of CuCl$_2$ 2H$_2$O and 1.25 g of 2,5-dimethyl cyclohexanone. Stirring is continued until all solids had dissolved. The container is pressurized with oxygen, and allowed to sit at room temperature for 18 hours. The methanol solvent is removed by rotary evaporator and the product extracted in ether. The ether layer is concentrated. GLC analysis confirmed the presence of 1-cyano-2-methyl-5-ketohexane.

Certain representative embodiments of the present invention have been shown in detail for the purpose of more particularly illustrating the invention. It will be apparent to those of skill in the art that various changes and modifications can be made herein without departing from the scope and spirit of the invention.

What is claimed is:

1. A process for preparing a compound of the formula:

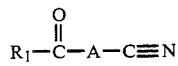

which comprises reacting a cycloalkanone compound of the formula:

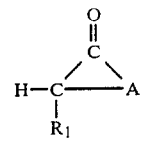

oxygen and ammonia in the presence of a catalytically effective amount of cupric cation and in an inert solvent wherein:
  R$_1$ is isopropyl, methyl, ethyl, propyl, methoxy, ethoxy, chloro, bromo, isobutyl, butyl, tert-butyl, pentyl, neopentyl, fluoro, amino, dimethylaminomethyl, or acetyl; and
  A is a divalent alkylene chain of the formula:

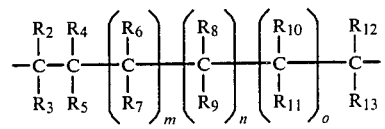

wherein:
  n, m and o are individually 1 or 0; and
  R$_2$ to R$_{13}$ are individually hydrogen, lower alkyl, lower alkoxy or phenyl wherein no more than three of said R$_2$ to R$_{13}$ substituents are other than hydrogen.

2. A process according to claim 1 wherein said oxygen, ammonia and cycloalkanone compounds are reacted in stiochiometric amounts.

3. A process according to claim 1 where said inert solvent is a hydroxy solvent.

4. A process according to claim 1 wherein said reacting temperature is from about 0° C. to about 200° C.

5. A process according to claim 1 wherein said reacting is carried out at autogenous pressure.

6. A process according to claim 1 wherein R$_1$ is methyl, ethyl, propyl, isopropyl, butyl, isobutyl, tert-butyl, pentyl or neopentyl.

7. A process according to claim 1 wherein n and m are 0, and O is 1.

8. A process according to claim 1 wherein no more than two of said R$_2$ to R$_{13}$ substituents are other than hydrogen.

9. A process according to claim 8 wherein no more than one of said R$_2$ to R$_{13}$ substituents is other than hydrogen.

10. A process according to claim 9 wherein each of R$_2$ to R$_{13}$ is hydrogen.

11. A process according to claim 1 wherein said solvent is methanol or ethanol.

12. A process according to claim 11 wherin said solvent is methanol.

13. A process according to claim 1 wherein said cupric cation is derived from cupric acetate, cupric octanoate, cupric chloride, cupric bromide, cupric nitrate and cupric sulfate.

14. A process according to claim 13 wherein said cupric cation is derived from cupric chloride.

* * * * *